United States Patent [19]

Hendler et al.

[11] Patent Number: 5,506,676
[45] Date of Patent: Apr. 9, 1996

[54] DEFECT DETECTION USING FOURIER OPTICS AND A SPATIAL SEPARATOR FOR SIMULTANEOUS OPTICAL COMPUTING OF SEPARATED FOURIER TRANSFORM COMPONENTS

[75] Inventors: Lawrence Hendler, Cupertino; Michael P. C. Watts, Portola Valley, both of Calif.

[73] Assignee: Pixel Systems, Inc., Cupertino, Calif.

[21] Appl. No.: 329,110

[22] Filed: Oct. 25, 1994

[51] Int. Cl.$^6$ .................................................... G01N 21/00
[52] U.S. Cl. ..................... 356/237; 356/73; 356/326; 356/367; 356/394; 250/559.09; 250/559.11; 250/559.41; 250/559.45; 250/559.46
[58] Field of Search ....................... 356/237, 429–431, 356/392, 394, 73, 326, 367, 336, 335; 250/562, 572, 559.09, 559.11, 559.41, 559.45, 559.46

[56] References Cited

U.S. PATENT DOCUMENTS

| | | | |
|---|---|---|---|
| 4,330,205 | 5/1982 | Murakami et al. | 356/237 |
| 4,330,775 | 5/1982 | Iwamoto et al. | 356/237 |
| 4,806,774 | 2/1989 | Lin et al. | 356/237 |
| 4,929,081 | 5/1990 | Yamamoto et al. | 356/354 |
| 5,046,847 | 9/1991 | Nakata et al. | 356/430 |
| 5,067,812 | 11/1991 | Sugimura et al. | 356/237 |
| 5,098,191 | 3/1992 | Noguchi et al. | 356/237 |
| 5,172,000 | 12/1992 | Scheff et al. | 356/237 |
| 5,264,912 | 11/1993 | Vaught et al. | 356/237 |
| 5,274,434 | 12/1993 | Monoka et al. | 356/237 |
| 5,276,498 | 1/1994 | Galbraith et al. | 356/237 |
| 5,289,260 | 2/1994 | Miyazaki et al. | 356/237 |
| 5,379,150 | 1/1995 | Miyazaki et al. | 356/237 |
| 5,410,400 | 4/1995 | Shishido et al. | 250/572 |

OTHER PUBLICATIONS

Lawrence H. Lin and Allen M. Carroll, "High–Speed Inspection of LCD Panels," Insystems, San Jose, CA., Jun. 19, 1991, pp. 79–82.

*Primary Examiner*—Frank Gonzalez
*Assistant Examiner*—Jason D. Eisenberg
*Attorney, Agent, or Firm*—Skjerven, Morrill, MacPherson, Franklin & Friel; David T. Millers; David E. Steuber

[57] ABSTRACT

High speed pattern and defect detection in flat panel displays, integrated circuits, photo mask reticles, CRT color masks, printed circuit boards, and any other patterned devices, regular or irregular, uses analog optical computing. Using appropriate illumination and optics, the Fourier transform of the image of a device under test is formed. The Fourier transform components of an ideal pattern are compared to the Fourier transform components of a measured pattern, and differences in relative intensities of the spatial components indicate a defect. A spatial separator is used to direct different components of the Fourier transform in different directions for parallel, simultaneous measurement and analysis. Utilizing Statistical Process Control, and properly comparing the different Fourier transform components, the defect is partially classified. Optical image processing is done in real time at the speed of light. Image acquisition at video rates is not a requirement, therefore detection can be performed on the fly while scanning the device under test.

24 Claims, 4 Drawing Sheets

DEFECT DETECTION USING FOURIER OPTICS AND A SPATIAL SEPARATOR FOR SIMULTANEOUS OPTICAL COMPUTING OF SEPARATED FOURIER TRANSFORM COMPONENTS

BACKGROUND OF THE INVENTION

1. Field of the Invention

This invention relates to systems which use optical Fourier computing to detect and classify defects in patterns.

2. Description of Related Art

Inspecting a patterned device is typically performed in one of three ways: (1) manually inspecting the device with the naked eye or with some enlarging lens or microscope; (2) digitizing an image of the device and digitally processing the image to detect defects; and (3) optically decomposing an image of the device with a Fourier transforming lens which forms a Fourier transform of the image, and a spatial filter which blocks light expected from a defect-free device and transmits light which would indicate a defect. Frequently, systems which optically form a Fourier transform also form an image from the light transmitted by the spatial filter, digitize the image, and perform defect characterization by digital computing.

Fourier optical inspection for defects is known in the art and described for example in: U.S. Pat. No. 4,330,205, to Murakami et al., for inspecting flat surfaces; U.S. Pat. No. 4,330,775, to Iwamoto et al., for inspecting periodic patterned surfaces; U.S. Pat. No. 4,806,774, to Lin et al., for inspecting integrated circuit patterns on wafers; U.S. Pat. No. 5,098,191, to Noguchi et al., for inspecting mask reticles. All these patents discuss different aspects of Fourier optical inspection for defect detection.

U.S. Pat. No. 5,264,912, to Vaught et al., describes broad band light sources for the purpose of Fourier optical inspection.

Many spatial filter designs are also known in the art. Specifically U.S. Pat. No. 4,929,081, to Yamamoto et al., describes an erasable optical space modulator; U.S. Pat. No. 5,172,000, to Scheff et al., describes a standard spatial filter for defect detection; U.S. Pat. No. 5,276,498, to Galbraith et al., describes an adaptive spatial filter based on liquid crystal light modulator used in a scanning detector system; and U.S. Pat. No. 5,289,260, to Miyazaki et al. describes a controlled filter spot on a photosensitive plate.

All of the above referenced patents are incorporated by reference herein in their entirety.

The prior art, including above referenced patents, have used spatial filters which block a first portion of light generated by the optics, and transmit a second portion of the light. The second portion of the light is of interest, and typically corresponds to light generated by defects. However, by blocking the first portion of light, information about a device being tested is lost, which can make some defects undetectable or make characterization of a defect more difficult. Accordingly, detecting and characterizing defects may require time consuming additional testing of the device.

SUMMARY OF THE INVENTION

In accordance with this invention, optical computing is performed by a Fourier transformer and a spatial separator. The Fourier transformer converts an initial light pattern from a device under test into a light pattern representing the Fourier transform of the initial pattern, and the spatial separator separates spatial frequency components of the Fourier transform pattern. The separated Fourier components can be separately and simultaneously measured. This provides more information about the device more quickly than the prior art defect detection systems which block some Fourier transform components. Statistical process control (SPC) is used to detect and classify a variety of defects and anomalies in the device based on the separated frequency components.

The device under test may be a flat panel display, integrated circuit, plastic sheet, printed paper, photo mask reticle, CRT color mask, printed circuit board, coatings on a plate, or any other regularly or irregularly patterned device or blank substrate. The device could also be a system in motion such as a fiber spinner having threads in high speed motion which form what appears to be a stationary pattern.

The Fourier transformer is typically a converging lens or series of lenses. The spatial separator separates spatial frequency components of the Fourier transform by directing different components in different directions to allow parallel measurements of multiple portions of the Fourier transform pattern of the device. Multiple measurements can then be compared to each other and to expected values utilizing SPC techniques.

Embodiments of the spatial separator in accordance with this invention include fixed and adaptive spatial separators. In alternative embodiments, a fixed spatial separator includes: a transparent substrate having mirrored areas which reflect selected Fourier transform components back to a beam splitter; a contoured substrate with mirrored areas fixed at different angles relative to incidence of light from Fourier transform optics; and a substrate having areas ruled with holographic or conventional diffraction gratings which diffract light representing selected Fourier components.

An adaptive spatial separator has a programmable or changeable separation pattern that can be changed for testing different devices, different patterned regions on a given device, or batch-to-batch and lot-to-lot differences in the same device. One embodiment of the adaptive spatial separator is an array of programmable micromirror devices. The detector system can additionally include a system for forming an image of the Fourier transform for a defect-free device and generating from the image a configuration for an adaptive filter which will separate portions of the Fourier transform indicating a defect from portions indicating a defect-free devise. The configuration can be stored or "learned" by the detector and used for later testing.

BRIEF DESCRIPTION OF THE DRAWINGS

Use of the same reference symbols in different figures indicates similar or identical items.

DETAILED DESCRIPTION

This invention provides systems and methods for using optical computation and statistical post processing to recognize patterns and/or defects on a device under test. The optical computation transforms an initial light pattern from the device into a light pattern which represents the Fourier transform of the initial pattern. A lens or series of lenses acts as a Fourier transformer which produces the Fourier transform pattern from the initial pattern. A spatial separator separates different components of the Fourier transform by directing light from different regions of Fourier transform pattern in different directions where the separated Fourier components can be measured in parallel. The measured Fourier components are then compared statistically to each other and expected values which include historical performance and fixed cut-off values to determine if the measured pattern matches an expected pattern.

In an example application where the device is a patterned substrate, measured Fourier components are compared to components expected for a defect-free patterned substrate to determine the existence and type of defects on the substrate. Statistical process control (SPC) of the measured components can detect and classify a variety of defects and anomalies in the patterned substrate. Blank substrates have a null pattern and can be tested similarly. Illustrations of devices that can be tested according to this invention include, but are not limited to, flat panel displays, integrated circuits, plastic sheets, printed paper, photo mask reticles, cathode ray tube (CRT) color matrices, printed circuit boards, or any other regularly or irregularly patterned devices or blank substrates.

Figure 1:
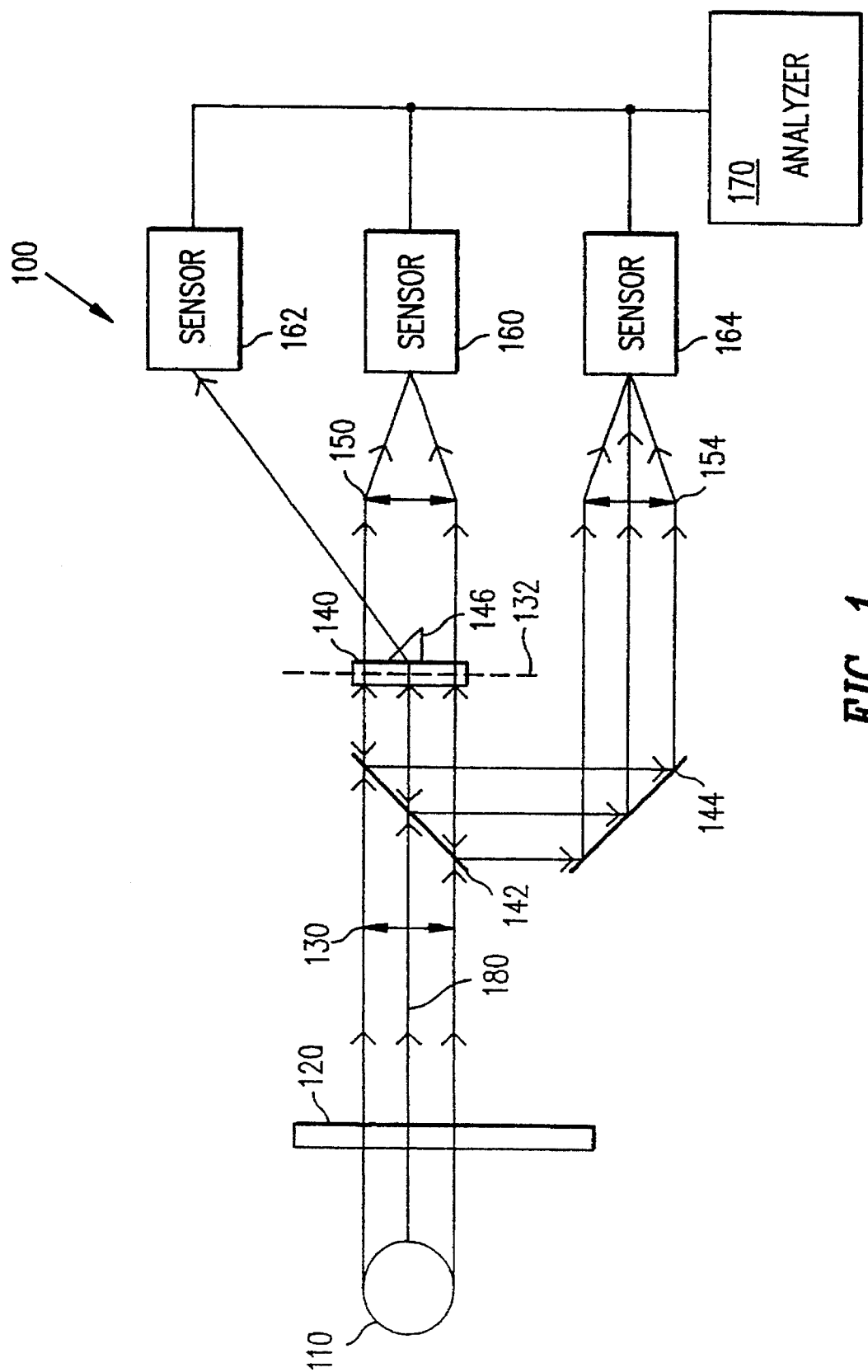
FIG. 1 shows a block diagram of a defect detection system in accordance with an embodiment of this invention.

FIG. 1 shows a block diagram of a pattern or defect detector 100 in accordance with an embodiment of this invention. Detector 100 includes an illumination system 110 and conventional Fourier transform optics 130 which generates a light pattern representing the Fourier transform of a pattern on a device under test 120. In detector 100, device 120 is partly transparent, and illuminating system 110 transmits light through a portion of device 120 to Fourier transform optics 130.

Figure 2:
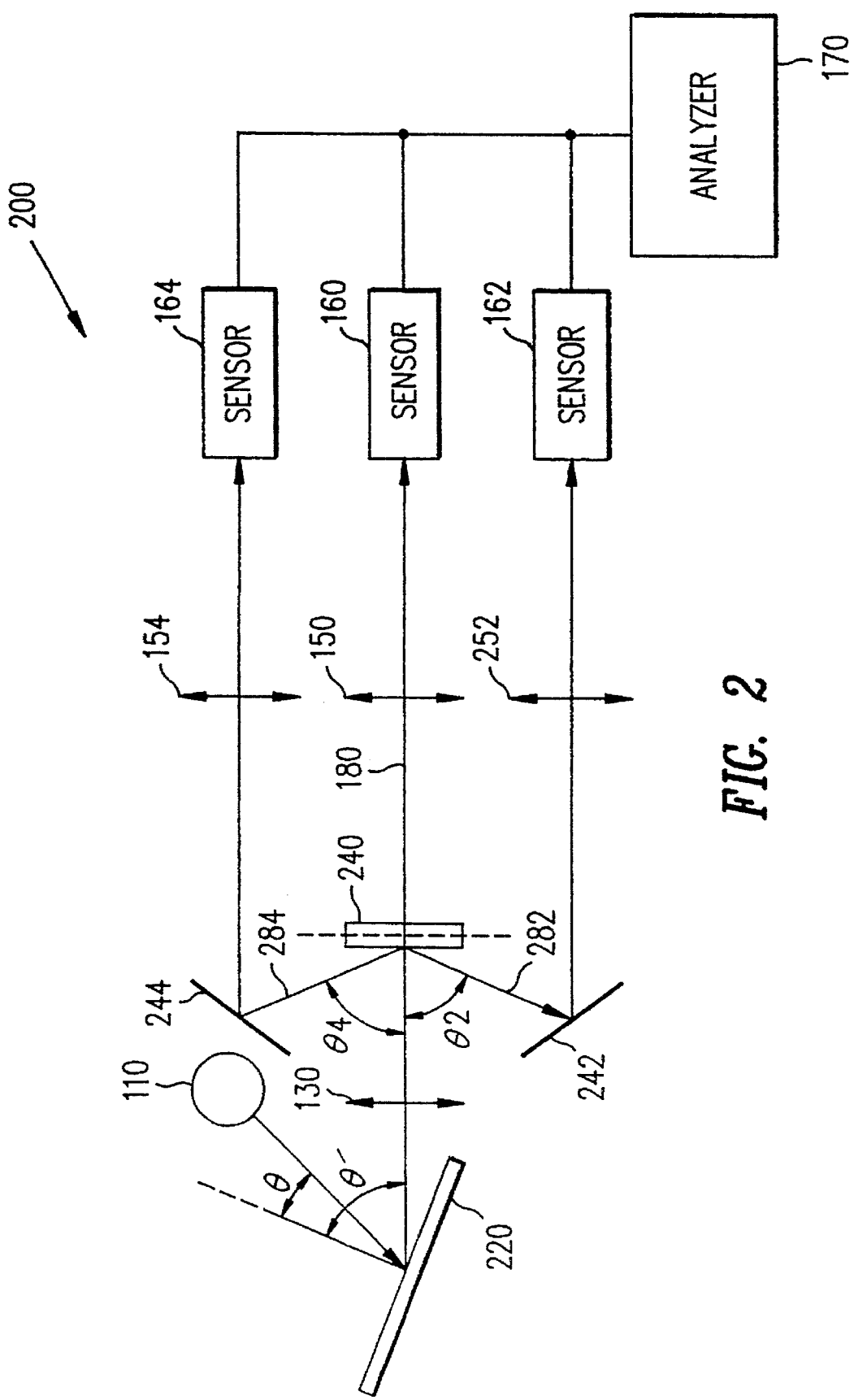
FIG. 2 shows a block diagram of a defect detection system in accordance with another embodiment of this invention.

In an alternative pattern or defect detector 200 shown in FIG. 2, illuminating system 110 reflects light from a device under test 220 which may or may not be transparent. An incidence angel Θ of light on device 220, from illuminating system 110 and an observation angle Θ' of Fourier transform optics 130 can be selected to provide bright field light pattern where most light reflected from device 220 enters Fourier transform optics 130 or dark field light pattern where most light from device 220 is reflected away from Fourier transform optics 130. The embodiment of FIG. 2 shows angles Θ and Θ' which provide a dark field pattern.

Illumination system 110 provides light which in alternative embodiments is continuous or pulsed mode, single wavelength, multiple wavelength, or continuous spectrum, coherent or non-coherent light. Illumination systems for providing such light are well known in the art and include one or more lasers and sources of noncoherent light such as a tungsten halogen bulb with and without color filters. Additionally, a polarizer may be added to light source 110 to provide light with a known polarization. In an alternative embodiment, light source 110 can be eliminated or not used, if device 120 emits light as, for example, a CRT, plasma, or field emission display could.

Device 120 is movable relative to illumination system 110 and Fourier transform optics 130. Fourier transform optics 130 images areas of device 120 in a step-and-repeat process or continuous scanning mode. Fourier transform optics 130 is a conventional lens or series of lenses which forms a light pattern in a Fourier plane 132 which is the Fourier transform of the light pattern from device 120. If transform optics 130 is a convex lens, for example, Fourier plane 132 coincides with the focal point of the lens. Light from Fourier transform optics 130 passes through a conventional beam splitter (half silvered mirror) 142 before reaching a spatial separator 140.

Fourier transforms correspond one-to-one with the pattern transformed. Accordingly, comparing the Fourier transform pattern to an ideal or expected Fourier transform pattern indicates whether the pattern on device 120 is as expected or desired. For example, a defect-free pattern on device 120 generates a defect-free Fourier transform pattern that has light intensity profile with bright regions and dark regions. If the pattern on device 120 is not the defect-free pattern, the Fourier transform pattern differs from the defect-free Fourier transform pattern. Typically, some expected dark regions are no longer dark, and the intensity in the expected bright regions changes.

Light in the expected bright regions is sometimes referred to herein as the ordered portion of the Fourier transform. This terminology "ordered" is used because patterned devices tend to generate Fourier transform patterns having discrete bright spots, and the bright spots can be ordered according to distance from the center of the pattern. Light in the central portion (zeroth order) of the Fourier transform pattern is referred to herein as the DC component. Light in the expected dark regions is sometimes referred to herein as the non-ordered portion.

Spatial separator 140 can be tailored according to the defect-free pattern, to separate Fourier components of the ordered portion from Fourier components of the non-ordered portion. Light intensities are measured and compared to expected values to determine whether device 120 has a defective pattern. Spatial separator 140 need not separate the non-ordered portion from the ordered portion of the Fourier transform but instead can separate Fourier transform components in any manner that facilitates analysis or defect detection or identification. Parallel intensity measurements can measure the ordered portion of the Fourier transform, the non-ordered portion of the Fourier transform, the DC component of the Fourier transform, or any other combination or subset of the Fourier transform components.

Spatial separator 140 includes a transparent substrate with reflective surfaces positioned appropriately to reflect certain spatial components of the Fourier transform back nearly along the optical axis 180 of Fourier transform optics 130. Spatial separator 140 may be formed using conventional mirror fabrication techniques such as silvering a glass substrate and then masking and etching to leave selected silvered regions surrounded by transparent regions.

The pattern of silvered regions to be formed in a particular spatial separator 140 can be determined by calculating the Fourier transform of a defect-free pattern or by imaging the actual Fourier transform pattern of a defect-free device 120. For example, a data base can record the patterns on working devices, and then a Fourier transform of an average recorded pattern can be calculated using well known mathematics. The portions of the calculated Fourier transform having an intensity above a predetermined threshold can be printed and used as the mask which defines silvered regions of spatial separator 140. Alternatively, Fourier transform optics can produce a Fourier transform pattern of a defect-free device, and the Fourier transform pattern can be photographed and used for the mask in the manufacture of spatial separator 140.

Figure 3A:
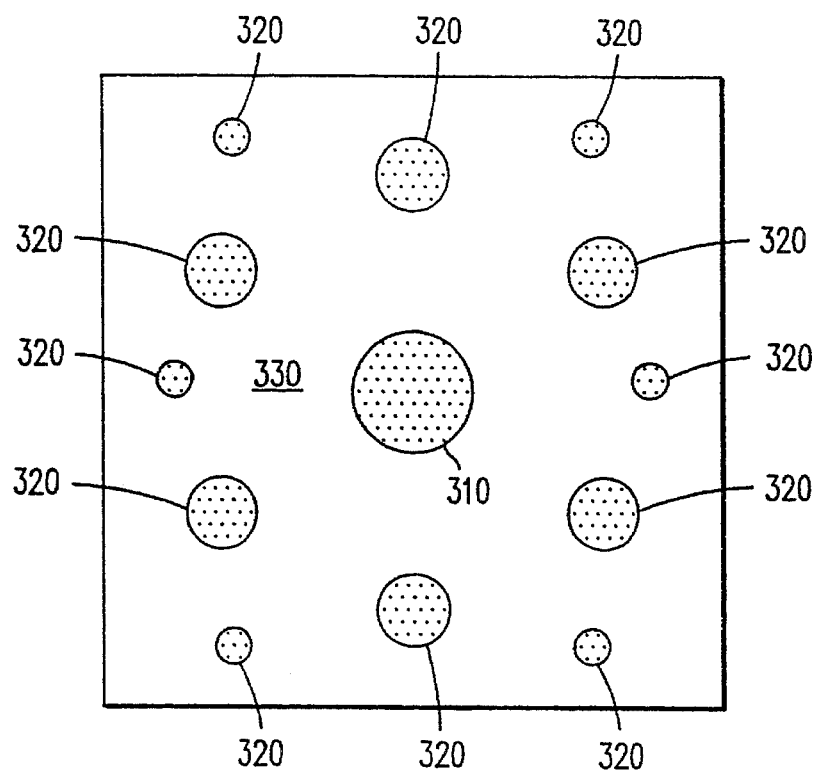
FIGS. 3A and 3B show example patterns of spatial separators in accordance with the embodiments of FIGS. 1 and 2 respectively.

FIG. 3A shows an example of spatial separator 140 which has reflective regions 320 that reflect part of the ordered portion of the light in a selected defect-free Fourier transform pattern. A region 330 of spatial separator 140 is transparent and transmits the non-ordered portion through spatial separator 140. The DC component is incident on region 310. In alternative embodiments, region 310 can be reflective, transparent, or opaque. When region 310 is reflective, the DC component is combined with the rest of the ordered portion reflected by regions 320. If desired, region 310 (and/or any of reflective regions 320) may be replaced by an opaque region to reduce the total intensity of the reflected light and improve the signal-to-noise ratio when detecting variations in intensity. In detector 100, region 310 of spatial separator 140 is transparent and transmits the DC component to a prism 146 which refracts the DC component.

The non-ordered portion is transmitted through spatial separator 140 and focused by an integrating lens 150 into a sensor 160. Sensor 160 measures the intensity of the transmitted light but could also measure properties such as frequency or polarization. In one embodiment, sensor 160 characterizes the total intensity the non-ordered portion from the tested area of device 120 as a single measured value. Other measured values from other areas of device 120 determined during scanning provide a map of an image of device 120. In an alternative embodiment, integrating lens 150 forms an image from the transmitted light, and sensor 160 provides an array of measured values for each area of device 120 tested. Since sensor 160 measures the non-ordered portion of the Fourier transform, high measured values in the image of device 120 indicate the location of defects.

Sensor choice and sensor geometries are driven by a number of considerations. Sensor rise time defines the maximum number of areas that can be tested in a given time and therefore, the scanning speed of detector 100. For a tested area width of 100 μm and a scan speed of 10 in/sec, a rise time of $100 \times 10^{-6}$ m/(10 in/sec×0.0254 m/in) or 400 μsec is required. Photosensors are commercially available which are orders of magnitude faster this. Sensor geometries and aperture size are also driven by the angular dispersion of light from the spatial separator. The angular dispersion determines the required numerical aperture of sensor 160 and the relative positions of sensors 160, 162, and 164 to avoid light from a particular Fourier component from reaching the wrong sensor.

Beam splitter 142 reflects part of the light from spatial separator 140, onto a mirror 144 which directs light into an integrating lens 154 for a sensor 164. Mirror 144 and integrating lens 154 are only an example of one device for directing light into sensor 164. Many other devices such as lens and fiber optics could be employed. Alternatively, sensor 164 can be repositioned to directly receive light from beam splitter 142. Sensor 164 measures a property such as intensity, frequency, or polarization which is typically but not necessarily the same property as sensor 160 measures.

To separate the DC component from other Fourier transform components, region 310 (FIG. 3A) of spatial separator 140 is transparent, and a prism 146 is located behind region 310 to refract the DC component into a third sensor 162. Alternatively, a conventional transmissive grating or holographic grating can replace prism 146 and diffract light to detector 162.

Typically, sensors 160, 162, and 164 operate in parallel to increase the throughput of detector 100 and provide information about three separate sets of Fourier transform components. In an alternative embodiment of the invention where region 310 is reflective, a second beam splitter can replace mirror 144 or be placed in series with beam splitter 142 to allow spatial filtering and separation of the DC component from the light reflected by spatial separator 140. The second beam splitter could also be used to separate Fourier components other than the DC component.

Detector 200 of FIG. 2 contains an alternative spatial separator 240 which reflects different sets of Fourier transform components along different angles $\Theta 2$ and $\Theta 4$. Mirrors 242 and 244 direct the sets of components to sensors 162 and 164 as shown by light rays 282 and 284 respectively. Alternatively, sensors 162 and 164 can be positioned to receive the light directly, or other optical systems can be used to direct rays 282 and 284 to sensors 162 and 164. FIG. 2 shows reflected light rays 282 and 284 which are coplanar with each other and optical axis 180 of Fourier transform optics 130. Alternatively, optical axis 180 and light ray 282 defining a different plane from optical axis 180 and light ray 284 may provide a more compact geometry for sensors 160, 162, and 164.

To provide the different angles of reflection, spatial separator 240 may have a contoured surface with mirrored regions at different angles relative to the optical axis 180. Such a spatial separator could be made by selectively etching or machining different portions of a substrate and forming mirrored regions at different angles relative to optical axis 180.

Another type of spatial separator 240 has local, regularly spaced diffraction gratings in different regions, and the gratings diffract light at angles which depend on the line spacing of the grating. A reflective grating could be used to reflect light rays 282 and 284 as shown in FIG. 2. A blazed grating may be used to increase the intensity of light in light rays 282 and 284 at angles $\Theta 2$ and $\Theta 4$. In an alternative embodiment, one or more transmissive gratings diffract light transmitted through spatial separator 240. Angular deflection of monochromatic light by a regularly spaced grating is given by the following equation.

$$d \sin \lambda = m \theta \tag{1}$$

where d is the spacing in the grating, $\lambda$ is the wavelength of the light, and m is the order of diffraction.

Yet another spatial separator 240 is made by holographically forming local gratings on different regions of spatial separator 240. Holographically formed gratings are sinusoidal in nature, and have a single diffraction order (m=1) but otherwise obey equation (1). Accordingly, for monochromatic light, the diffraction angles $\Theta 2$ and $\Theta 4$ are solely dependent on the grid spacing d in the regions which cause the diffraction. The plane containing optical axis 180 and light ray 282 or 284 depends on orientation of the grating. Grid spacing and orientation can be controlled in the manufacture of holographic gratings by setting the relative angle between the object and reference beams to the desired diffraction angle $\Theta 2$ or $\Theta 4$. Specific regions of spatial separator 240 can be manufactured with specific grating spacings to control the angle at which each component of the Fourier transform is diffracted.

Figure 3B:
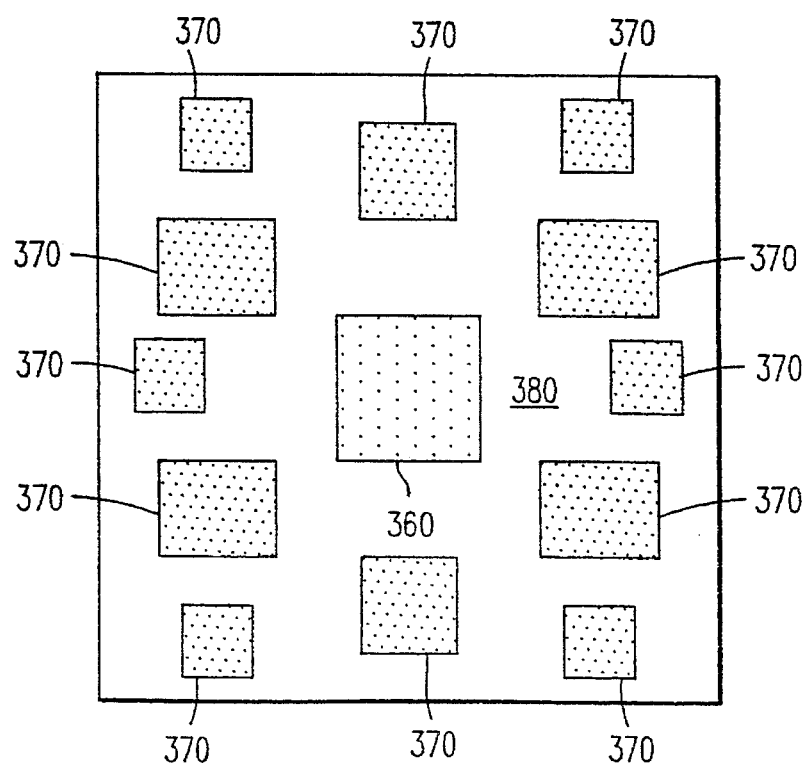

FIG. 3B shows an exemplary configuration of spatial separator 240 which separates a Fourier transform into three separate components using regions 360, 370, and 380 which direct light in different directions. Region 380 is transparent and transmits light representing the non-ordered portion of a selected Fourier transform. Region 360 corresponds to the DC component of the Fourier transform and contains a holographic grating which diffracts light at angle $\Theta 2$. Regions 370 correspond to the ordered portion and contain holographic gratings which diffract light at angle Θ4. For the example of Θ2 and Θ4 equal to 30° and 45° and monochromatic light at 632.8 nm wavelength, equation (1) indicates the grating in region 360 has 790 lines per mm (30 degrees), and the gratings in regions 370 have 1117 lines per mm (45 degrees). In an alternative embodiment, region 380 can contain a holographic diffraction grating with a third diffraction angle if sensor 160 is properly positioned or if a mirror or other optical system is provided to direct light from region 380 to sensor 160.

For multiple wavelength light, angular dispersion of the diffracted light occurs. Angular dispersion for a diffraction grating is the change in diffraction angle per the change in wavelength and is expressed as follows:

$$\frac{\Delta\theta}{\Delta\lambda} = \frac{m}{d\cos\theta} \qquad (2)$$

Equation (2) is the derivative of the angle given by the grating equation (1) with respect to wavelength. Equation (2) shows that as the diffraction Θ angle grows, the angular dispersion increases and shows that the smaller grating spacing causes greater angular dispersion. To measure all the light reflected, sensors 162 and 164 must have a numerical aperture large enough to receive the dispersed light.

Spatial separator 240 can also be made programmable by forming an array of controllable reflective devices such as Texas Instruments' Digital Micromirror Device. The digital micromirror device is a micromechanical device fabricated with an array of aluminum mirrors on a layer of addressable electrodes. Each electrode can be individually activated to provide a specific torsion to a hinge connected to the mirror. This torsion rotates the mirror a given amount, and light incident on the mirror is reflected in a direction which depends on the mirror's rotation. Individual micromirrors are about 25×25 µm so that a typical Fourier transform could be incident on as many as 2 million mirrors. Two million mirrors provide a high degree of control over the selected sets of Fourier components to be measured. In this embodiment, spatial separator 240 is programmed as an adaptive reflective spatial separator.

An adaptive spatial separator 240 facilitates defect inspection of non-uniformly patterned substrates, such as an integrated circuit die, because spatial separator 240 can be reprogrammed during the scanning operation as scanning moves to an area on the substrate having a different pattern. An adaptive separator also allows rapid change to different patterns and different products in a production line. Several spatial separator configurations can be stored in a memory of a control circuit which controls the orientation of each micromirror in an array forming the adaptive spatial separator. The configurations stored can be determined from a Fourier transform calculated from recorded patterns on defect-free devices or from digitized images of Fourier transform patterns formed by Fourier transform optics.

Figure 4:
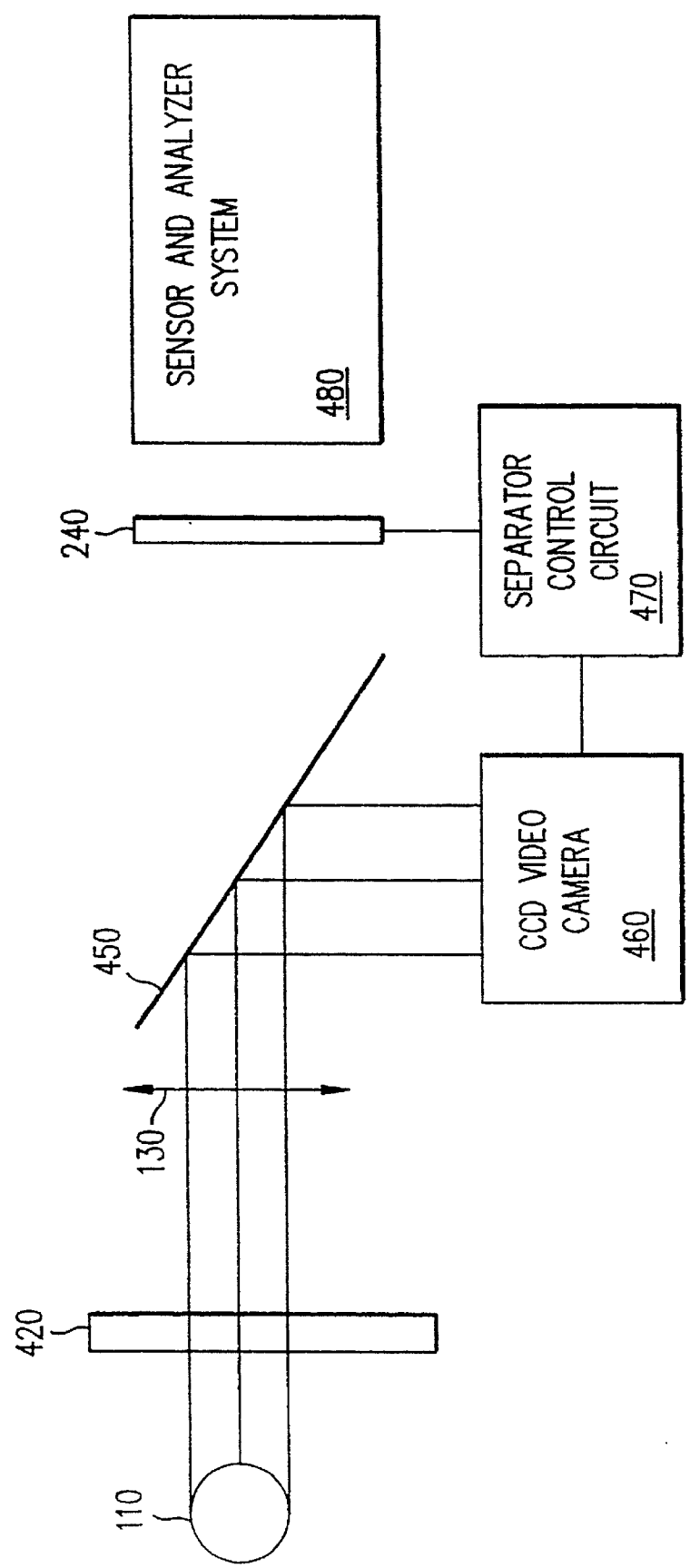
FIG. 4 shows a block diagram of a defect detection system having a subsystem for configuring an adaptive spatial separator in accordance with another embodiment of this invention.

FIG. 4 shows a block diagram of a detector system containing a subsystem for configuring adaptive spatial separator 240. The subsystem configures spatial separator 240 based on an Fourier transform pattern of a defect-free device 420. When defect-free device 420 is placed in the detector system, a reflector 450 in the optical path of light from Fourier transform optics 130 reflects light into a CCD (charge coupled device) camera 460 which may be for example a conventional video camera. Reflector 450 may include a half silvered mirror or other beam splitter which both transmits light to spatial separator 240 and reflects light to CCD camera 460. Reflector 450 may also be retractable so that reflector 450 can be removed from the optical path of Fourier optics 130 during testing of a device.

CCD camera 460 is positioned to produce an image of the Fourier transform pattern formed by Fourier transform optics 130. A separator control circuit 470 digitizes the image from CCD camera 460 and determines a light intensity incident on each micromirror in spatial separator 240 for a defect-free Fourier transform pattern. The ordered and non-ordered portions can be separated by causing micromirrors which receive more light to reflect light in a first direction and micromirrors which receive less light to reflect light in a second direction. The DC component can be identified as a region closest to the center of the pattern and reflected in a third direction. Once the desired pattern is determined, a retractable reflector 450 can be removed from the optical path, and values for the separated Fourier components can be measured and processed using sensor and analyzer system 480 which is similar or identical to the systems described in regard of FIGS. 1 and 2. Alternatively, a reflector 450 that is a beam splitter can be left in the optical path during determination of expected values and during testing of a device.

An analyzer 170 as shown in FIGS. 1 and 2 performs a statistical comparison of measured values from sensors 160, 162, and 164 with expected values. Analyzer 170 includes a computer such as a personal computer with a conventional hardware interface for receiving measurements from sensors 160, 162, and 164 and software for analyzing the measurements. Alternatively, dedicated hardware can implement the desired analysis.

Each measurement is correlated with corresponding expected values specific to a selected defect-free Fourier transform. The expected values can be established by experiment or calculation to provide clear cut-off values indicating or classifying a defect. The expected values can also be determined from historical performance which indicates a statistical norm for the measured values based on a record of previous measurements. The significance of each measurement depends on the difference from the expected value and the deviation of the measurement from the mean difference of all measurements from corresponding expected values.

Tests of this type are called hypothesis tests and are well known in the art. Statistical process control (SPC) enables real time hypothesis testing of measurements. The choices of Fourier components separated, properties measured, and analysis will depend on the device being tested. For the example of a flat panel display, appropriate measurements and analysis can differentiate among single pixel defects, multi-pixel defects, area non uniformities, thickness variations, reflective variations, protrusions, sub pixel defects, foreign particulates 3 µm or larger (killer particles), and polarization variances.

If device 120 is a flat panel display and each area tested contains a single pixel of the flat panel display, a flag can be set for each set of Fourier components measured such as the non-ordered portion, the ordered portion, and the DC component of the Fourier transformation which shows a statistically significant variation from the expected value. A significant variation in the non-ordered portion of the Fourier transform as measured by sensor 160 indicates the pixel in the area tested is defective. No flag for the non-ordered portion, a flag for large deviation in the DC component, and no flag for non DC components of the ordered portion could indicate a transmitivity or reflectivity variation. Comparing the sum of the intensities of the ordered and non-ordered portion of the Fourier transform can indicate a defect without classifying the defect. Multiple wavelength comparisons for the DC component could be used as a thickness or color measurement.

Another example is a particulate on an integrated circuit. Using a dark field illumination, edges of particulates reflect light into the Fourier transform optics. An adaptive reflective spatial separator separates the ordered portion of the Fourier transform from the non-ordered portion, so that an image formed with the non-ordered portion indicates the edges of the particulate.

In addition to the statistical intensity differentiation, a polarometer which measures polarization of the Fourier components or spectrometer which measures the relative intensities of different wavelengths of light can be added to sensors 160, 162, or 164. With proper analysis, detectors in accordance with this invention can act as a variety of tools such as an optical densitometer, a colorimeter, or a reflectometer. Also, as described above, the ordered portion or the non-ordered portion of the Fourier transform can be used to respectively reconstruct a device image or a defect image. These tools enable the system to perform analytical inspections for defects which might not be discovered from intensity measurements alone.

Although the present invention has been described with reference to particular embodiments, the description is only an example of the invention's application and should not be taken as a limitation. Various adaptations and combinations of features of the embodiments disclosed will be apparent to those skilled in the art and are within the scope of the present invention as defined by the following claims.

We claim:

1. A detector comprising:

Fourier transform optics positioned to form a Fourier transform pattern of light from a device under test;

a spatial separator positioned to receive light from the Fourier transform optics, the spatial separator having a plurality of regions including a first region which receives light from a first component of the Fourier transform pattern and directs that light in a first direction and a second region which receives light from a second component of the Fourier transform pattern and directs that light in a second direction which differs from the first direction; and a sensor system which separately measures light directed in the first direction by the spatial separator and light directed in the second direction by the Spatial separator.

2. The detector of claim 1, wherein:

the spatial separator comprises a substrate the first region comprises a portion of the substrate that reflects light from the substrate; and the second region comprises a portion of the substrate that transmits light through the substrate.

3. The detector of claim 2, wherein the first region is in a Fourier plane of the Fourier transform optics.

4. The detector of claim 3, wherein the spatial separator further comprises a beam splitter positioned to transmit light from the Fourier transform optics to the first and second regions, and wherein the first region reflects light back to the beam splitter.

5. The detector of claim 1, wherein the spatial separator further comprises a holographic grating positioned in a Fourier plane, the first region is a portion of the holographic grating having a first line spacing which diffracts light in the first direction, and the second region is a portion of the holographic grating having a second line spacing which diffracts light in the second direction.

6. The detector of claim 1, wherein:

the spatial separator comprises an array of mirrors;

the first region comprises a first set of mirrors which are at a first angle relative to an optical axis of the Fourier transform optics, the first set of mirrors reflecting light in the first direction; and the second region comprises a second set of mirrors which are at a second angle relative to the optical axis of the Fourier transform optics, the second set of mirrors reflecting light in the second direction.

7. The detector of claim 6, wherein each mirror in the array is rotatably mounted.

8. The detector of claim 7, wherein each mirror in the array comprises a digital micromirror.

9. The detector of claim 1, further comprising a light source which projects light through the device under test to the Fourier transform optics.

10. The detector of claim 1, further comprising a light source which projects light which is reflected from the device under test to the Fourier transform optics.

11. The detector of claim 1, wherein the device under test comprises a light source which projects light to the Fourier transform optics.

12. The detector of claim 1, further comprising an analyzer which compares values measured by the sensor system to values expected for a defect-free pattern.

13. The detector of claim 1, wherein the sensor system further comprises a plurality of photodetectors.

14. The detector of claim 1, wherein the sensor system further comprises:

optics which forms an image of the device under test using light from a first set of regions of the spatial separator; and a sensor which measures light intensity at a series of points in the image.

15. The detector of claim 1, wherein the sensor system further comprises a plurality of spectrometers.

16. The detector of claim 1, wherein the sensor system further comprises a plurality of polarometers.

17. The detector of claim 1, wherein:

the Fourier transform optics forms a light pattern having an ordered portion and a non-ordered portion, the non-ordered portion resulting from defects in the device under test;

the first region is shaped and positioned to receive the ordered portion of the light from the Fourier transform optics; and the second region is shaped and positioned to receive an non-ordered portion of the light from the Fourier transform optics.

18. The detector of claim 17, wherein the sensor system comprises:

a first photodetector;

a first integrating lens positioned to focus the ordered portion the light into the first detector;

a second photodetector; and a second integrating lens positioned to focus the non-ordered portion the light into the second detector.

19. A method for detecting difference between a first pattern and a second pattern, comprising:

imaging light which is in the first pattern with Fourier transform optics to form a light pattern having spatial components which indicate a Fourier transform of the first pattern;

directing a first spatial component of the light pattern in a first direction;

directing a second spatial component of the light pattern in a second direction;

measuring the first and the second spatial components in parallel to simultaneously determine a first value which describes the first spatial component and a second value which describes the second spatial component; and comparing the first and second values to third and fourth values indicating corresponding Fourier components of the second pattern.

20. A detector comprising:

Fourier transform optics positioned to image light from a device under test; and an adaptive spatial separator positioned to receive light from the Fourier transform optics, the spatial separator comprising an array of individually addressable devices which each direct incident light in a programmable direction.

21. The detector of claim 20, further comprising a control circuit which controls the direction into which each individually addressable device directs light.

22. The detector of claim 21, further comprising an imaging system which forms an image of the Fourier transform pattern of a device, wherein the control circuit further comprises means for determining a configuration for the adaptive spatial separator from the image formed by the imaging system.

23. The detector of claims 22, wherein the imaging system comprises:

a charge couple device; and a reflector which reflects light from the Fourier transform optics, to the charge coupled device, wherein the charge coupled device uses light reflected by the reflector to form an image of a Fourier transform pattern formed by the Fourier transform optics.

24. The detector of claim 23, wherein the reflector is movably mounted to be inserted and removed from an optical path of light from the Fourier transform optics.

* * * * *